US012419727B2

(12) United States Patent
Liu et al.

(10) Patent No.: US 12,419,727 B2
(45) Date of Patent: Sep. 23, 2025

(54) ORAL IRRIGATOR

(71) Applicant: FLY CAT ELECTRICAL CO., LTD., Guangdong (CN)

(72) Inventors: Xinquan Liu, Guangdong (CN); Yong Tang, Guangdong (CN)

(73) Assignee: FLY CAT ELECTRICAL CO., LTD., Guangdong (CN)

( * ) Notice: Subject to any disclaimer, the term of this patent is extended or adjusted under 35 U.S.C. 154(b) by 814 days.

(21) Appl. No.: 17/730,594

(22) Filed: Apr. 27, 2022

(65) Prior Publication Data
US 2023/0025032 A1  Jan. 26, 2023

(30) Foreign Application Priority Data
Jul. 21, 2021  (CN) .......................... 202121667499.3

(51) Int. Cl.
*A61C 17/02* (2006.01)
*A61K 8/22* (2006.01)

(52) U.S. Cl.
CPC .......... *A61C 17/02* (2013.01); *A61C 17/0202* (2013.01); *A61K 8/22* (2013.01); *A61K 2800/83* (2013.01)

(58) Field of Classification Search
CPC . A61C 17/00; A61C 17/02–032; A61C 19/06; Y02E 60/36; A61K 8/22
See application file for complete search history.

(56) References Cited

U.S. PATENT DOCUMENTS

| | | | | |
|---|---|---|---|---|
| 5,928,505 A | * | 7/1999 | Inakagata | A61C 17/02 320/108 |
| 2007/0212665 A1 | * | 9/2007 | Jimenez | A61N 1/322 433/215 |
| 2009/0114605 A1 | * | 5/2009 | Salama | C25B 9/00 210/748.19 |
| 2015/0238755 A1 | * | 8/2015 | Fregoso | A61C 1/07 433/32 |
| 2017/0334750 A1 | * | 11/2017 | Nitta | C02F 1/4672 |
| 2018/0279761 A1 | * | 10/2018 | Haddad | A46B 15/003 |
| 2020/0179088 A1 | * | 6/2020 | Yuan | A61C 17/0217 |
| 2022/0228277 A1 | * | 7/2022 | Shiue | C25B 9/65 |

* cited by examiner

*Primary Examiner* — Rachel T Sippel
*Assistant Examiner* — Jacqueline M Pinderski
(74) *Attorney, Agent, or Firm* — Brooks Kushman P.C.

(57) ABSTRACT

An oral irrigator includes: an irrigator body, and a generator arranged inside the irrigator body. The irrigator body includes: a water tank, a nozzle, and a driver. The water tank is used to accommodate an electrolyte. The generator is used to electrolyze the electrolyte to generate ozone water and hydrogen-rich water. The electrolyte of the water tank is driven by the driver to enter the generator, electrolyzed in the generator, such that a resulting electrolyzed ozone water and hydrogen-rich water are sprayed out from the nozzle of the irrigator body. In this way, it is solved the technical problem that the existing oral irrigator only uses a water flow for physical cleaning.

15 Claims, 5 Drawing Sheets

ORAL IRRIGATOR

CROSS-REFERENCE TO RELATED APPLICATIONS

Pursuant to 35 U.S.C. § 119 and the Paris Convention, this application claims the benefit of Chinese Patent Application No. 202121667499.3 filed Jul. 21, 2021, the contents of which are incorporated herein by reference.

TECHNICAL FIELD

The present application relates to the field of oral care products, and more particularly to an oral irrigator.

BACKGROUND

Oral irrigator is a home oral care product that uses high-pressure pulsed water to remove food residues trapped in gaps between teeth that toothbrushes and dental flosses cannot access, so as to effectively clean dental plaques, improve gingivitis, reduce gum bleeding, freshen breath, and so on. As people pay more attention to personal oral health, oral irrigator is becoming more and more popular.

A basic principle of the oral irrigator is to use a pump to extract water from a water tank to a nozzle, where the high-pressure pulsed water is prayed out to clean the teeth and the oral cavity.

However, existing oral irrigators only utilize a high-pressure pulsed water flow for flushing and cleaning, which only involves physical cleaning, and fails to provide more efficient oral care.

SUMMARY

It is an object of the present application is to provide an oral irrigator, which aims to solve the technical problem that the existing oral irrigator only uses a water flow for physical cleaning.

To achieve the above object, the following technical solutions are adopted by the present application:

An oral irrigator is provided. The oral irrigator comprises: an irrigator body, and a generator arranged inside the irrigator body. The irrigator body comprises: a water tank, a nozzle, and a driving assembly. The water tank is configured to accommodate an electrolyte. The generator is configured to electrolyze the electrolyte to generate ozone water and hydrogen-rich water. The electrolyte of the water tank is driven by the driving assembly to enter the generator, electrolyzed in the generator, such that a resulting electrolyzed ozone water and hydrogen-rich water are sprayed out from the nozzle of the irrigator body.

In an embodiment of the present application, the electrolyte is water. The generator comprises: at least one cathode plate, at least one anode plate, and a casing enclosing the at least one cathode plate and the at least one anode plate. The at least one cathode plate and at least one anode plate are spaced apart from one another and arranged alternately. The at least one cathode plate and the at least one anode plate are in electrical connection with a negative electrode and a positive electrode of a power source assembly of the irrigator body, respectively. The casing is provided with a water inlet and a water outlet.

In an embodiment of the present application, the number of the at least one cathode plate is two, and the number of the at least one anode plate is one; and the one anode plate is arranged between the two cathode plates.

In an embodiment of the present application, a distance between adjacent cathode plate and anode plate is smaller than or equal to 5 mm.

In an embodiment of the present application, an area of each of the at least one cathode plate and the at least one anode plate is smaller than or equal to 20 square centimeters.

In an embodiment of the present application, both of the at least one cathode plate and the at least one anode plate are made of a titanium alloy.

In an embodiment of the present application, the driving assembly comprises: a pump and a motor adapted to the pump. The generator is arranged between the water tank and the pump, the water inlet communicates with the water tank, and the water outlet communicates with the inlet of the pump; or alternatively, the generator is arranged between the pump and the nozzle, the water inlet communicates with an outlet of the pump, and the water outlet communicates with the nozzle.

In an embodiment of the present application, in case that the generator is arranged between the water tank and the pump, the generator is assembled at a top of the water tank, the water inlet of the generator is provided with a connecting pipe, and the connecting pipe is arranged within the water tank.

In an embodiment of the present application, the generator further comprises an assembling body. The assembling body and the casing form an integrated structure. The assembling body is arranged at the top of the water tank, and is configured to assemble the pump and the motor.

In an embodiment of the present application, the assembling body defines therein an assembling recess. The pump and the motor are in connection with assembling pieces. The assembling pieces are arranged within the assembling recess to connect the pump, the motor, and the water tank to be an integrated structure. A housing is sleeved outside the pump and the motor.

Advantages of the oral irrigator according to embodiments of the present application are summarized as follows:

Compared with the prior art, a generator for producing ozone water/hydrogen-rich water is arranged within the irrigator body of the present application. The generator is able to directly and rapidly prepare the ozone water and the hydrogen-rich water by using a method of water electrolysis at a low voltage, and the prepared ozone water and hydrogen-rich water can be sprayed out of the irrigator body through the nozzle to reach the oral cavity of the human body.

The role of ozone water is to quickly and effectively kill viruses, bacteria, and harmful microorganisms in the teeth and the oral cavity, such as tuberculosis, *Escherichia coli*, gonococcus, typhoid *bacillus*, etc. The ozone water can also produce a sterile water, which is harmless to the human body. In addition, the ozone water can remove halitosis, bleach the tooth discoloration, and remove the dirt.

The role of hydrogen-rich water is to eliminate excessive active oxygen free radicals in the human body and improve the sub-health state of the human body. The hydrogen-rich water also has strong antioxidant capacity and can improve the oxidative damage to the human body in the process of various diseases.

BRIEF DESCRIPTION OF DRAWINGS

In order to illustrate the technical solutions in the embodiments of the present application more clearly, the following will briefly introduce the drawings needed in the description of the embodiments or the existing technology. Obviously.

Figure 1:
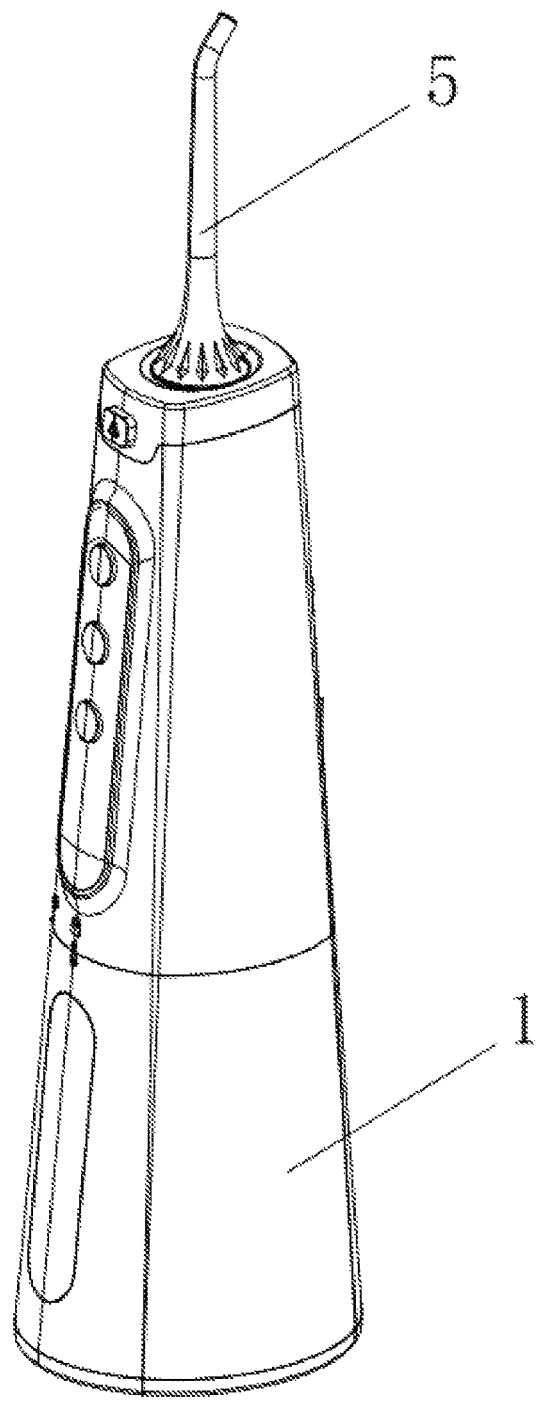
FIG. 1 is a schematic diagram of a structure of an oral irrigator in accordance with an embodiment of the present application.
Figure 2:
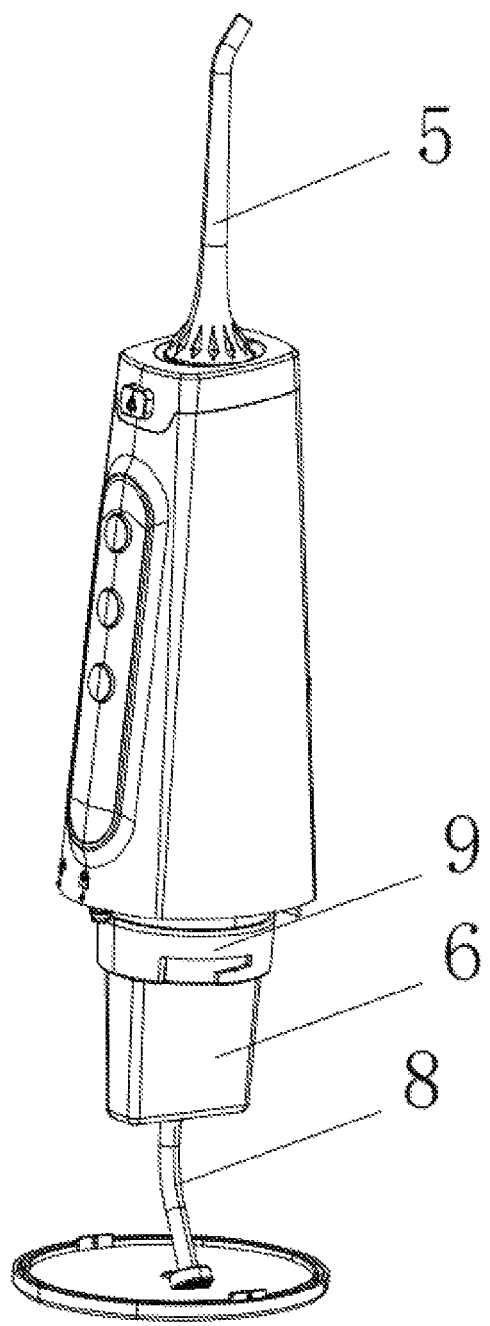
FIG. 2 is a schematic diagram of an internal structure of the water tank in FIG. 1.

In the drawings, the following reference numerals are adopted:

1: Water tank; 2: Cathode plate; 3: Anode plate; 4: Water inlet; 5: Nozzle; 6: Casing; 7: Water outlet; 8: Connection pipe; 9: Assembling body; 10: Pump; and 11: Motor.

DETAILED DESCRIPTION OF THE EMBODIMENTS

In order to make the technical problem to be solved, technical solutions, and beneficial effects of the present application more comprehensible, the present application will be further described in detail below with reference to the accompanying drawings and embodiments. It should be understood that the embodiments described here are merely used to illustrate the present application, and are not intended to limit the present application.

It should be noted that when an element is referred to as being "fixed to" or "disposed/provided on" another element, it may be directly or indirectly on the other element. When an element is referred to as being "connected to" another element, it may be directly or indirectly connected to the other element.

In addition, the terms "first" and "second" are only used for descriptive purpose, and cannot be understood as indicating or implying relative importance or implicitly indicating the number of indicated technical features. Thus, the features defined with "first" and "second" may explicitly or implicitly include one or more of these features. In the description of the present application, the term "a/the plurality of" means two or more, unless otherwise specifically defined. The word "several" means one or more, unless otherwise specifically defined.

In the description of the present application, it should be understood that direction or position relationship indicated by terms "center," "length," "width," "upper," "thickness," "lower," "front," "back," "left," "right," "vertical," "horizontal," "top," "bottom," "inner," "outer" and the like, are based on the orientation or position relationship shown in the drawings, which are merely used for the convenience of describing the present application and simplifying the description, rather than indicating or implying that the device or element referred to must have a specific orientation, be constructed and operated in a specific orientation, it thus cannot be understood as a limitation to the present application.

In the description of the present application, it should be noted that, unless otherwise clearly specified and defined, the terms "installed/mounted," "coupled to", and "connected to/with" should be understood in a broad sense. For example, it may be a fixed connection or a detachable connection, or an integrated connection. It may be mechanically connected or electrically connected. It may be directly connected or may be indirectly connected through an intermediate medium. It may be an internal communication between two components or an interaction relationship between two components. For those of ordinary skill in the art, the specific meaning of the above-mentioned terms in the present application can be understood according to specific circumstances.

As shown in FIGS. 1-5, the present application provides a specific embodiment of an oral irrigator. The oral irrigator comprises an irrigator body and a generator arranged inside the irrigator body. The irrigator body comprises: a water tank 1, a nozzle 5, and a driving assembly. The water tank 1 is configured to accommodate an electrolyte, and the generator is configured to electrolyze the electrolyte to generate ozone water and hydrogen-rich water. The electrolyte of the water tank 1 is driven by the driving assembly to enter the generator, electrolyzed in the generator, such that a resulting electrolyzed ozone water and hydrogen-rich water are sprayed out from the nozzle 5 of the irrigator body.

Specifically, a basic structure of the irrigator body comprises: the water tank 1, the driving assembly, the nozzle 5, and a power supply assembly. The power supply assembly can be an accumulator that can be charged and discharged. The driving assembly provides power to the driving assembly, and the water is sprayed out the water tank 1 via the nozzle 5 to flush the oral cavity of the human body. In this embodiment, the generator is arranged in the water tank 1, and the water in the water tank 1 can be electrolyzed at a low voltage when the generator is energized, thereby generating the ozone water and the hydrogen-rich water, so that the ozone water and the hydrogen-rich water are sprayed from the nozzle 5 under the action of the driving assembly, so that the ozone water and the hydrogen-rich water can be used to clean the oral cavity of the human body.

In this embodiment, since the ozone water and the hydrogen-rich water are generated under the action of low-voltage electrolysis, the oral cavity of the human body can be cleaned by the ozone water and the hydrogen-rich water.

The generated ozone water has a care effect on the oral cavity of the human body in that the ozone water can quickly and effectively kill virus bacteria such as tuberculosis, *Escherichia coli*, gonococcus, typhoid *bacillus*, etc. as well as harmful microorganisms in the teeth and the oral cavity. The ozone water can also produce a sterile water, which is good for human body and is harmless. In addition, the ozone water can remove halitosis, bleach the tooth discoloration, and remove the dirt.

The generated hydrogen-rich water has a care effect on the oral cavity of the human body in that the hydrogen-rich water can eliminate excessive active oxygen free radicals in the human body and can improve the sub-health state of the human body. The hydrogen-rich water also has strong anti-oxidant capacity and can improve the oxidative damage to the human body in the process of various diseases.

Figure 4:
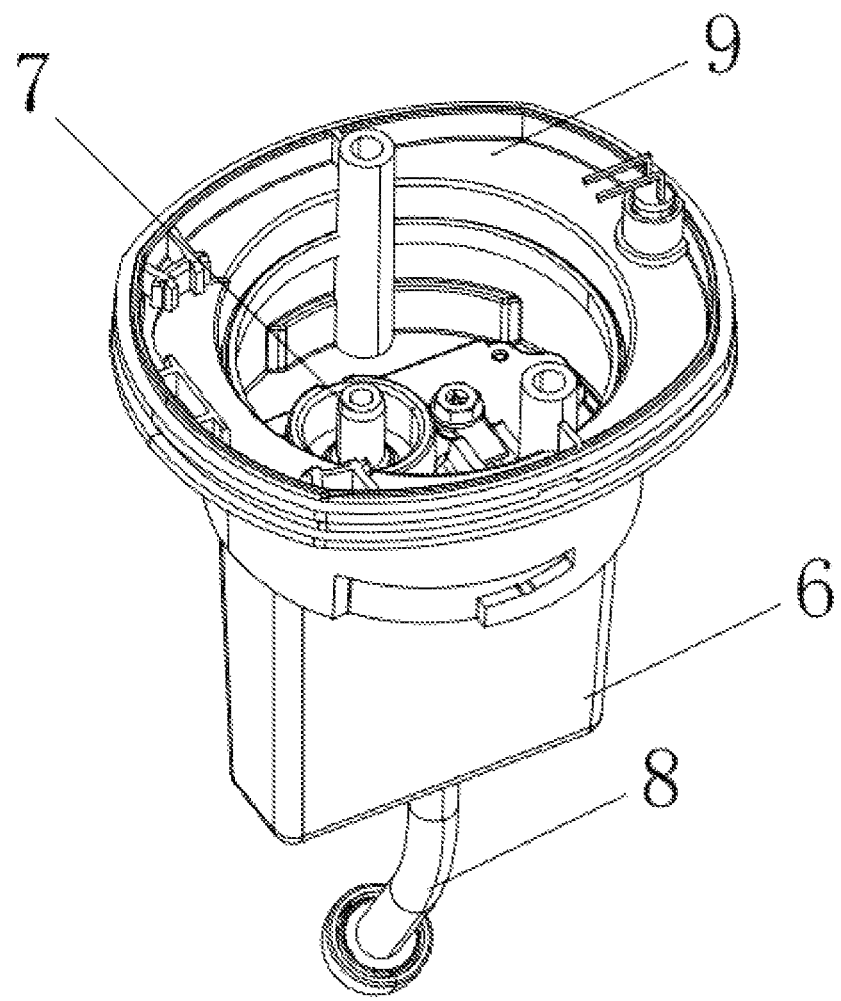
FIG. 4 is a schematic diagram of a casing and an assembling body of FIG. 3.
Figure 5:
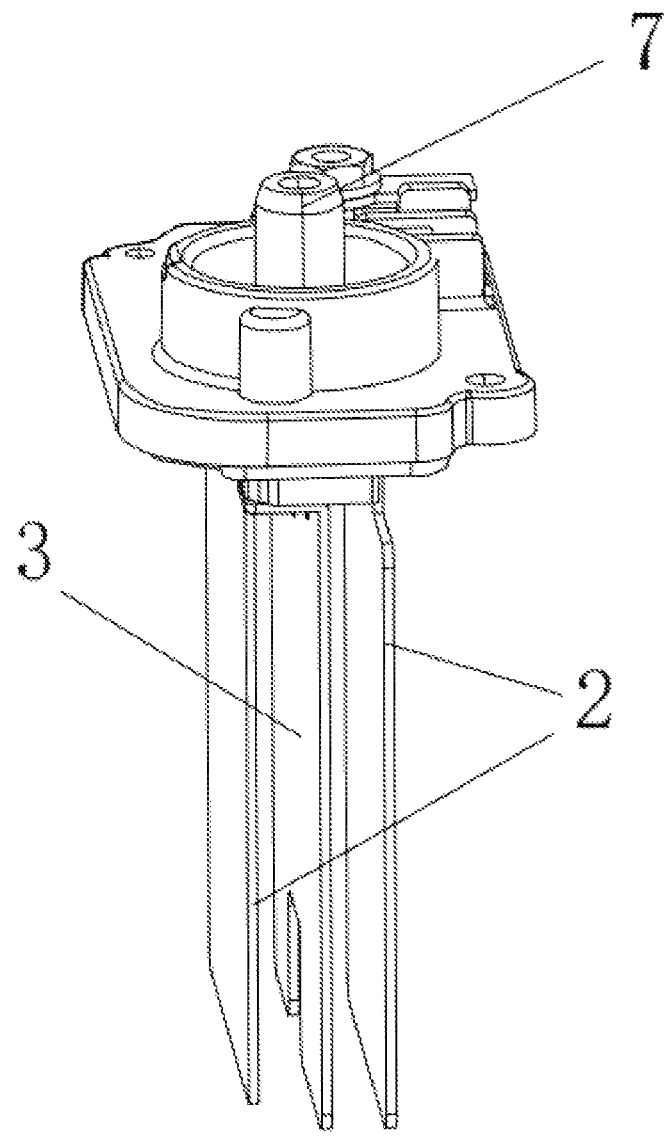
FIG. 5 is a schematic diagram of an internal structure of a casing of FIG. 4.

As shown in FIGS. 4-5, in an embodiment of the present application, the working process of the generator is that the at least one cathode plate 2 and the at least one anode plate 3 are energized to electrolyze water to generate the ozone water and the hydrogen-rich water. The at least one cathode plate 2 and the at least one anode plate 3 are spaced apart from one another and arranged alternately. The water located between the at least one cathode plate 2 and the at least one anode plate 3 is electrolyzed. In order to ensure that the electrolyzed ozone water and hydrogen-rich water will not be dispersed in the entire water tank 1, but can be directly enter the nozzle 5, in this embodiment, the casing 6 is provided accordingly. The cathode plate 2 and the anode plate 3 are enclosed within the casing 6, so that the ozone water and the hydrogen-rich water produced are all accommodated within the casing 6 and are prevented from being dispensed to the entire water tank 1. In addition, the casing 6 has a water inlet 4 and a water outlet 7. Driven by the pump 10, the water in the casing 6 flows out from the water outlet 7, and at this time, the water flows from the water tank 1 into the casing 6 via the water inlet 4, and the newly introduced water is electrolyzed in the casing 6 again. In this way, not only is the continuous electrolysis ensured, but also the ozone water and the hydrogen-rich water are ensured to go directly to the nozzle 5 rather than being dispersed.

In this embodiment, the at least one cathode plate 2 and the at least one anode plate 3 can electrolyze water to produce the ozone water and the hydrogen-rich water, while the casing 6 encloses the cathode plate 2 and anode plate 3 to form a fixed space, thus, the ozone water and the hydrogen-rich water within the fixed space will not be dispersed, and are ensured to be sprayed out from the nozzle 5.

Specifically, the at least one cathode plate 2 and the at least one anode plate 3 both adopt plate-like structures and are arranged side by side. A gap is provided between the adjacent cathode plate 2 and anode plate 3, and the water flowing into the gap is electrolyzed. The shape of the casing 6 is similar to those of the at least one cathode plate 2 and the at least one anode plate 3. For example, the shapes of the at least one cathode plate 2 and the at least one anode plate 3 are plate-like and rectangular or square, the casing 6 is also rectangular or square in shape, and has a flat structure, so that the water in the casing 6 is near the electrode plates, thus most of the water can be electrolyzed and then pumped out, which can increase the concentration of the ozone water and the hydrogen-rich water.

As shown in FIG. 5, in an embodiment of the present application, two cathode plates 2 and one anode plate 3 are provided. The anode plate 3 is located between the two cathode plates 2 so that the water between the one anode plate 3 and the two cathode plates 2 is electrolyzed. The water entering through the water inlet 4 may flow between the one anode plate 3 and the two cathode plates 2, so as to be electrolyzed. Or alternatively, two anode plates 3 and one cathode plate 2 may be provided, specifically, one cathode plate 2 is located between the two anode plates 3, the arrangement of which may also realize the electrolysis.

In this embodiment, it is provided two cathode plates 2 and one anode plate 3, the number of electrode plates is not very large. This is because the amount of water in the water tank 1 for flushing teeth is relatively small, it is not necessary to provide too many electrode plates. Moreover, the power supply component has a limited power storage, thus only two cathode plates 2 and one anode plate 3 may be enough. In another embodiment, only one cathode plate 2 and one anode plate 3 can be adopted, the number of the electrode plates can be selected according to actual needs.

Specifically, an input condition for the low-voltage electrolysis power supply may be a DC power supply below 12-20 V and a constant current below 600 mA. In the application of the electrolysis structure in the oral irrigator, the cathode and anode plates do not need to be a short-circuit prevention structure.

Further, a distance between the adjacent cathode plate 2 and anode plate 3 is smaller than or equal to 5 mm.

A maximum distance between the adjacent cathode plate 2 and anode plate 3 is only 5 mm, such that only a thin layer of water exists between the adjacent anode plate 2 and anode plate 3, which ensures the water between the adjacent anode plate 3 and anode plate 2 be fully and thoroughly electrolyzed. Moreover, the water body exchange is realized by the flow of the water body, and the water body is continuously electrolyzed, which can achieve thorough electrolysis of a large amount of the water body, thereby producing a higher concentration of the ozone water and the hydrogen-rich water.

Due to the small distance between the adjacent cathode plate 2 and the anode plate 3, the water body can be fully electrolyzed, so that the water body can be continuously electrolyzed to produce high-concentrated ozone water and hydrogen-rich water.

In an embodiment, an area of each cathode plate 2 and each anode plate 3 is smaller than or equal to 20 square centimeters. The cathode plate 2 and anode plate 3 have a large effective electrolysis area, which can generate a large amount of ozone water and hydrogen-rich water, and thus increasing the concentration of the ozone water and the hydrogen-rich water in the water body.

Further, both the cathode plate 2 and the anode plate 3 are made of a titanium alloy. The titanium alloy has a very high use temperature, and can work for a long time at a temperature of 450-500° C. The titanium alloy has strong corrosion resistance in a humid environment, and has strong resistance to pitting, acid corrosion, and stress corrosion, furthermore, the titanium alloy has excellent corrosion resistance on chloride, chlorine organic products, nitric acid, and sulfuric acid. Therefore, the use of titanium alloy can ensure the use effect, prolong the service life, and avoid the repeated replacement of the electrode plate.

Figure 3:
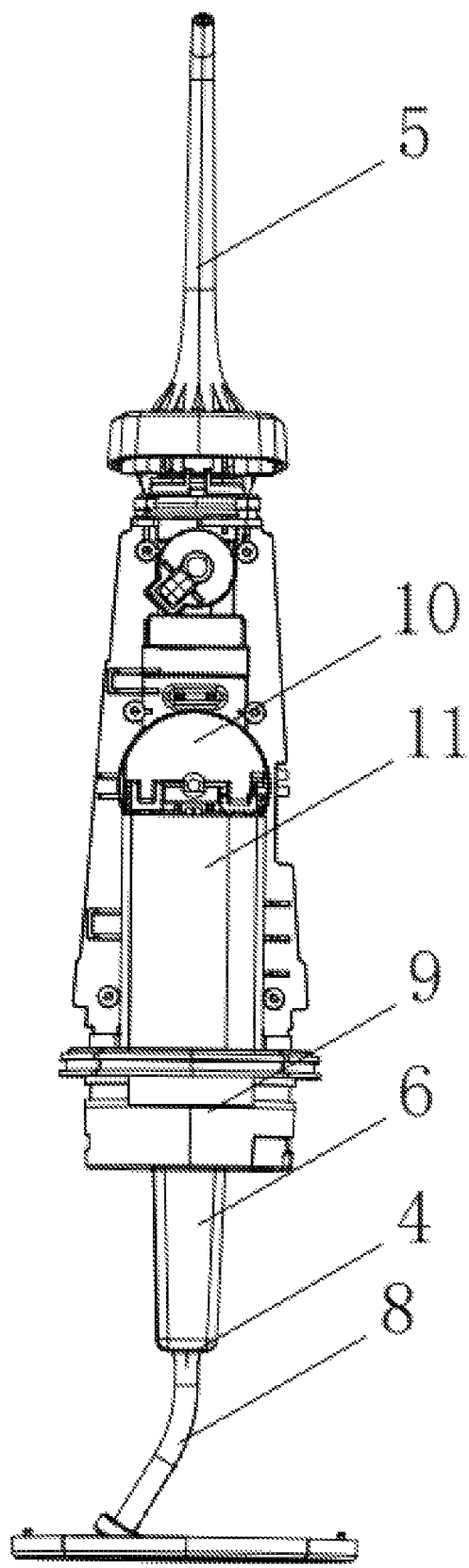
FIG. 3 is a schematic diagram of an internal structure of an oral irrigator provided by an embodiment of the present application.

As shown in FIG. 3, in an embodiment, the driving assembly comprises: a pump 10 and a motor 11. The motor 11 is configured to drive the pump 10 to rotate, and the pump 10 is configured to drive the ozone water and the hydrogen-rich water to flow to the nozzle, where the ozone water and the hydrogen-rich water are sprayed out. The arrangement position of the generator is optional, specifically, as long as the generator is arranged in a flow path of the water from the water tank 1 through the pump 10 to the nozzle 5. That is, in case that the generator is arranged between the water tank 1 and the pump 10, the water inlet 4 communicates with the water tank 1, and the water outlet 7 communicates with the inlet of the pump 10; and in case that the generator is arranged between the pump 10 and the nozzle 5, the water inlet 4 communicates with an outlet of the pump 10, and the water outlet 7 communicates with the nozzle 5.

In this embodiment, the arrangement position of the generator is optional and can be selected according to actual needs, which increases the operability and convenience of structural arrangement.

As shown in FIG. 3, preferably, in case that the generator is arranged between the water tank 1 and the pump 10, the generator is assembled at a top of the water tank 1, the water inlet 4 of the generator is provided with a connecting pipe 8, and the connecting pipe 8 is arranged within the water tank 1. When arranged between the water tank 1 and the pump 10, the generator is installed at the top of the water tank 1, that is, at the top within the water tank 1, which reduces the space occupied by the water tank 1. In addition, the form of the connecting pipe 8 is adopted, the connecting pipe 8 is connected at the water inlet 4 of the casing 6, and the connecting pipe 8 extends into the water tank 1, such that a large amount of water in the water tank 1 can be easily extracted, and it is avoided that the water in the water tank 1 cannot be extracted due to the drop in the water level.

As shown in FIGS. 3-4, further, when being arranged at the top of the water tank 1, the generator further comprises an assembling body 9, in addition the casing 6. That is, the assembling body 9 is arranged at the top of the casing 6. The assembling body 9 and the casing 6 form an integrated structure. The assembling body 9 is configured to seal the top of the water tank 1, and is configured to assemble the pump 10 and the motor 11 above the water tank 1, such that the water tank 1 and the upper structure are connected to form an integrated structure, thereby forming an integrated irrigator body.

In this embodiment, the top of the water tank 1 is sealed by the assembly 9 and used to assemble the pump 10 and the motor 11 in the upper structure, so that the water tank 1 and the upper structure are connected as a whole. Specifically, the pump 10 and the motor 11 are not directly arranged on assembly body 9, but are connected to the assembly body 9 through other connecting structures, which effectively enhances the integrity effect.

As shown in FIG. 4, further, the assembling body 9 defines therein an assembling recess. The assembling recess adopts a circular recess structure, with only a top thereof being open and a bottom thereof in connection with the casing 6. Because of the recess structure, assembling pieces can be provided therein. The assembling pieces are configured as components capable of supporting the pump 10 and the motor 11. The assembling pieces are inserted and connected within the recess structure to form an integrated structure. In addition, a housing is arranged outside the pump 10 and the motor 11, and connected with the water tank, thereby forming an overall relatively smooth surface of the oral irrigator.

The above descriptions are merely some preferred embodiments of the present application, and are not intended to limit the present application. Any modifications, equivalent replacements, and improvements made within the spirit and principle of the present application shall be included within the protection scope of the present application.

What is claimed is:

1. An oral irrigator, comprising:
   an irrigator body, comprising: a water tank, a nozzle, and a driver; and
   a generator, arranged inside the irrigator body; and
   wherein
   the water tank is configured to accommodate an electrolyte;
   the generator is configured to electrolyze the electrolyte to generate ozone water and hydrogen-rich water; and
   the electrolyte of the water tank is driven by the driver to enter the generator, electrolyzed in the generator to generate the ozone water and the hydrogen-rich water, such that the electrolyzed ozone water and the hydrogen-rich water are sprayed out from the nozzle of the irrigator body;
   the driver comprises: a pump and a motor adapted to the pump; and
   the generator is arranged between the water tank and the pump, a water inlet communicates with the water tank, and a water outlet communicates with an inlet of the pump, the generator is assembled at a top of the water tank, the water inlet of the generator is provided with a connecting pipe, and the connecting pipe is arranged within the water tank.

2. The oral irrigator of claim 1, wherein
   the electrolyte is water;
   the generator comprises: at least one cathode plate, at least one anode plate, and a casing enclosing the at least one cathode plate and the at least one anode plate; the at least one cathode plate and the at least one anode plate are spaced apart from one another and arranged alternately; and
   the at least one cathode plate and the at least one anode plate are in electrical connection with a negative electrode and a positive electrode of a power source assembly of the irrigator body, respectively; and
   the casing is provided with a water inlet and a water outlet.

3. The oral irrigator of claim 2, wherein a number of the at least one cathode plate is two, and a number of the at least one anode plate is one; and the one anode plate is arranged between the two cathode plates.

4. The oral irrigator of claim 2, wherein a distance between the at least one cathode plate and the at least one anode plate is smaller than or equal to 5 mm.

5. The oral irrigator of claim 2, wherein an area of each of the at least one cathode plate and the at least one anode plate is smaller than or equal to 20 square centimeters.

6. The oral irrigator of claim 2, wherein both of the at least one cathode plate and the at least one anode plate are made of a titanium alloy.

7. The oral irrigator of claim 2, wherein
   the generator further comprises an assembling body;
   the assembling body and the casing form an integrated structure; and
   the assembling body is arranged at the top of the water tank, and is configured to assemble the pump and the motor.

8. The oral irrigator of claim 7, wherein
   the assembling body defines therein an assembling recess;
   the pump and the motor are in connection with assembling pieces; and
   the assembling pieces are arranged within the assembling recess to connect the pump, the motor, and the water tank to be another integrated structure; and
   a housing is sleeved outside the pump and the motor.

9. The oral irrigator of claim 8, wherein a number of the at least one cathode plate is two, and a number of the at least one anode plate is one; and the one anode plate is arranged between the two cathode plates.

10. The oral irrigator of claim 8, wherein a distance between the at least one cathode plate and the at least one anode plate is smaller than or equal to 5 mm.

11. The oral irrigator of claim 8, wherein an area of each the at least one cathode plate and the at least one anode plate is smaller than or equal to 20 square centimeters.

12. The oral irrigator of claim 8, wherein both of the at least one cathode plate and the at least one anode plate are made of a titanium alloy.

13. The oral irrigator of claim 8, wherein
   a number of the at least one cathode plate is two, and a number of the at least one anode plate is one; and the one anode plate is arranged between the two cathode plates;
   a distance between the at least one cathode plate and the at least one anode plate is smaller than or equal to 5 mm;
   an area of each of the at least one cathode plate and the at least one anode plate is smaller than or equal to 20 square centimeters; and
   both of the at least one cathode plate and the at least one anode plate are made of a titanium alloy.

14. The oral irrigator of claim 1, wherein
   the generator further comprises an assembling body;

the assembling body and a casing of the generator form an integrated structure; and the assembling body is arranged at the top of the water tank, and is configured to assemble the pump and the motor.

15. The oral irrigator of claim 14, wherein the assembling body defines therein an assembling recess;

the pump and the motor are in connection with assembling pieces; and the assembling pieces are arranged within the assembling recess to connect the pump, the motor, and the water tank to be another integrated structure; and a housing is sleeved outside the pump and the motor.

* * * * *